(12) United States Patent
Kim et al.

(10) Patent No.: US 9,034,971 B2
(45) Date of Patent: May 19, 2015

(54) COMPOSITE SHEET AND DISPLAY SUBSTRATE USING SAME

(75) Inventors: Young Kwon Kim, Uiwang-si (KR); Sang Keol Lee, Uiwang-si (KR); Sung Han Im, Uiwang-si (KR); Seok Won Choi, Uiwang-si (KR); Sung Kook Kim, Uiwang-si (KR); Hyun Ae Jeon, Ansan-si (KR); Yun Joo Kim, Ansan-si (KR); Sang Yong Tak, Ansan-si (KR); Suk Yeon Park, Ansan-si (KR); Kyung Nam Kang, Ansan-si (KR); So Young Kang, Ansan-si (KR)

(73) Assignees: Cheil Industries Inc., Gum-si (KR); Korea Institute of Industrial Technology, Cheonan-si (KR)

( * ) Notice: Subject to any disclaimer, the term of this patent is extended or adjusted under 35 U.S.C. 154(b) by 0 days.

(21) Appl. No.: 14/116,963

(22) PCT Filed: May 7, 2012

(86) PCT No.: PCT/KR2012/003557
§ 371 (c)(1),
(2), (4) Date: Jan. 16, 2014

(87) PCT Pub. No.: WO2012/153957
PCT Pub. Date: Nov. 15, 2012

(65) Prior Publication Data
US 2014/0142248 A1    May 22, 2014

(30) Foreign Application Priority Data

May 12, 2011   (KR) ................. 10-2011-0044646

(51) Int. Cl.
| | |
|---|---|
| *B60C 1/00* | (2006.01) |
| *C08K 7/14* | (2006.01) |
| *C08L 63/00* | (2006.01) |
| *C08G 65/18* | (2006.01) |
| *C08G 65/22* | (2006.01) |
| *C07D 407/12* | (2006.01) |
| *C08J 5/24* | (2006.01) |

(52) U.S. Cl.
CPC . *C08K 7/14* (2013.01); *C08L 63/00* (2013.01); *C08G 65/18* (2013.01); *C08G 65/22* (2013.01); *C07D 407/12* (2013.01); *C08J 5/24* (2013.01); *C08J 2363/00* (2013.01)

(58) Field of Classification Search
USPC .......................................... 524/494
See application file for complete search history.

(56) References Cited

U.S. PATENT DOCUMENTS

| | | | |
|---|---|---|---|
| 6,166,101 A * | 12/2000 | Takami ................... | 522/168 |
| 6,770,737 B2 * | 8/2004 | Kakuchi et al. ......... | 528/406 |
| 2010/0277919 A1 * | 11/2010 | Okada et al. ............ | 362/249.02 |

* cited by examiner

*Primary Examiner* — Ling Choi
*Assistant Examiner* — Thuy-Ai Nguyen
(74) *Attorney, Agent, or Firm* — Christie, Parker & Hale, LLP

(57) ABSTRACT

A composite sheet of the present invention comprises an oxetane-epoxy-based compound, represented by chemical formula 1, as a binder.

10 Claims, 1 Drawing Sheet

COMPOSITE SHEET AND DISPLAY SUBSTRATE USING SAME

CROSS-REFERENCE TO RELATED APPLICATIONS

This application is a National Phase Patent Application and claims priority to and benefit of International Patent Application Number PCT/KR2012/003557, filed on May 7, 2012, which claims priority of Korean Patent Application Number 10-2011-0044646, filed on May 12, 2011, the entire contents of which are incorporated herein by reference.

TECHNICAL FIELD

The present invention relates to a composite sheet and a display substrate using the same. More particularly, the present invention relates to a composite sheet, which includes an oxetane-epoxy bifunctional compound having a specific structure as a binder to provide excellent flexibility while securing excellent properties in terms of heat resistance, crack resistance optical properties and processability, and a display substrate using the same.

BACKGROUND ART

A glass substrate having excellent thermal resistance, transparency and a low coefficient of linear expansion has been widely used as a substrate for liquid crystal display devices, organic EL display devices, color filters, solar cells, etc. Recently, plastic materials have attracted attention as an alternative to glass substrates for display devices to satisfy requirements, such as reduction in size, thickness and weight, excellent impact resistance, and flexibility.

Examples of materials recently used as such plastic substrates include polyethylene terephthalate (PET), polyether sulfone (PES), polyethylene naphthalate (PEN), polyarylate (PAR), polycarbonate (PC), polyimide (PI), and the like.

However, these materials can cause problems such as deflection of products and disconnection of wiring due to their considerably high coefficients of thermal expansion. In addition, although polyimide resin has a relatively low coefficient of thermal expansion, it is pointed out that the polyimide-based resin is not suitable for substrate materials due to very low transparency, high birefringence and moisture absorption.

To solve these problems, Japanese Patent Publication No. 2004-51960A discloses a transparent composite optical sheet made of an alicyclic epoxy resin containing an epoxy group, a bisphenol A epoxy resin, an acid anhydride curing agent, a catalyst, and glass fiber cloths.

Further, Japanese Patent Publication No. 2005-146258A discloses a transparent composite optical sheet made of an alicyclic epoxy resin containing an ester group, an epoxy resin with a dicyclopentadiene skeleton, an acid anhydride curing agent, and glass fiber cloths, and Japanese Patent Publication No. 2004-233851A discloses a transparent substrate made of a bisphenol A epoxy resin, a bisphenol A novolac epoxy resin, an acid anhydride curing agent, and glass fiber cloths.

However, the composite sheets disclosed in these patents have a glass transition temperature (Tg) within the range of 145° C. to 160° C., which is lower than a process temperature employed during manufacture of the same, and thus have low heat resistance and deteriorated processability.

In order to increase the glass transition temperature (Tg) of a composite sheet, a method of introducing a bulky aromatic structure into a binder has been proposed. However, in this case, the sheet has reduced flexibility and becomes rigid and thus may not be suitable for flexible substrates. In addition, due to increased viscosity, the sheet is deteriorated in solubility and wettability, and becomes brittle.

Therefore, there is a need for a novel composite sheet that has improved heat resistance without deterioration in flexibility and exhibits excellent wetting properties to glass fibers.

DISCLOSURE

Technical Problem

One aspect of the present invention is to provide a composite sheet having excellent properties in terms of flexibility, transparency, heat resistance and crack resistance, while ensuring excellent resistance to impact, tension, and bending.

Another aspect of the present invention is to provide a composite sheet having a low coefficient of thermal expansion and excellent light transmittance.

A further aspect of the present invention is to provide a composite sheet which has low viscosity, thereby providing excellent processability and wettability in preparation of a glass fiber composite.

Yet another aspect of the present invention is to provide a composite sheet which does not have a glass transition temperature (Tg) within a process temperature range, thereby providing excellent heat resistance.

Yet another aspect of the present invention is to provide a composite sheet enabling adjustment of curing rate.

Yet another aspect of the present invention is to provide a display substrate enabling reduction in size, thickness, weight and cost using the composite sheet.

Technical Solution

One aspect of the present invention relates to a composite sheet. The composite sheet includes an oxetane-epoxy compound, represented by Formula 1, as a binder:

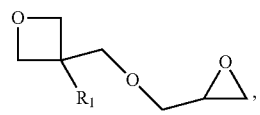

[Formula 1]

wherein $R_1$ is hydrogen, a methyl group, or an ethyl group.

The composite sheet may include a binder including the oxetane-epoxy compound, and a glass filler. In one embodiment, the composite sheet includes 100 parts by weight of the binder and about 40 parts by weight to about 300 parts by weight of the glass filler, preferably about 60 parts by weight to about 250 parts by weigh of the glass filler.

The glass filler may include at least one selected from the group consisting of glass fibers, glass fiber cloths, glass fabrics, non-woven glass fabrics, glass meshes, glass beads, glass powders, and glass flakes.

In one embodiment, the binder may further include a cationic polymerizable compound.

The cationic polymerizable compound may include at least one selected from the group consisting of epoxy group-containing compounds, oxetane group-containing compounds, vinyl ether group-containing compounds, and caprolactam group-containing compounds.

The difference in refractive index between the binder and the glass filler may be about 0.01 or less.

The oxetane-epoxy compound, represented by the Formula 1, may have a molecular weight/equivalent weight of a reactive functional group of about 110 g/eq or less, preferably about 100 g/eq or less.

In one embodiment, the composite sheet may further include a cationic initiator.

In one embodiment, the composite sheet may have a glass transition temperature of about 150° C. or more, preferably about 200° C. or more, more preferably about 250° C. or more. In another embodiment, the composite sheet may exhibit no glass transition point at about 350° C. or less (Tg-less properties).

Another aspect of the present invention relates to a display substrate including the composite sheet.

In one embodiment, the substrate has a coefficient of thermal expansion (a1) of about 30 ppm/° C. or less, preferably about 20 ppm/° C. or less, as measured using a TMA at 5° C./min from 30° C. to 250° C.

Advantageous Effects

The composite sheet according to the present invention has excellent flexibility, transparency and heat resistance while ensuring excellent impact resistance, tensile strength, bending resistance, etc. In addition, the composite sheet has a low coefficient of thermal expansion and excellent light transmittance. Further, the composite sheet has low viscosity, thereby providing excellent processibility and wettability in preparation of a glass fiber composite. Further, the composite sheet exhibits Tg-less properties within a process temperature range, thereby providing excellent heat resistance. Furthermore, the composite sheet permits adjustment of curing rate. A display substrate including the composite sheet permits reduction in size, thickness, weight, and cost.

BEST MODE

Figure 1:
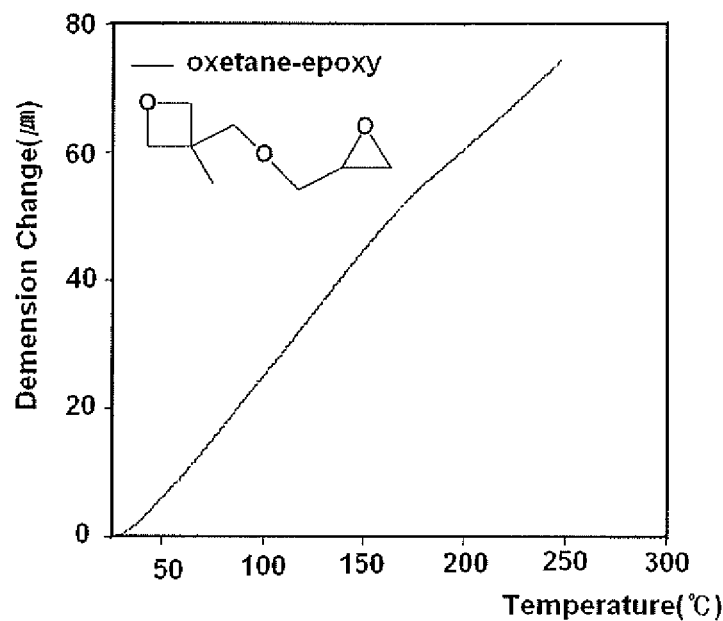
FIG. 1 shows a TMA graph of a composite sheet prepared in Example 1.

One aspect of the present invention relates to a composite sheet. The composite sheet includes a binder and a glass filler.

The binder includes an oxetane-epoxy compound represented by Formula 1:

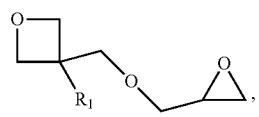
[Formula 1]

wherein $R_1$ is hydrogen, a methyl group, or an ethyl group.

As shown in Formula 1, the oxetane-epoxy compound according to the present invention has an asymmetric structure of a single oxetane group at one terminal thereof and an epoxy group at the other terminal thereof, and has a low molecular weight, thereby increasing a concentration of reactive functional groups within the composite sheet. This leads to high cross-linking density in curing and thus increases hardness, thereby providing improved heat resistance and exhibiting no inflection point of glass transition temperatures at about 250° C. or less. In addition, in the case of using such an oxetane-epoxy compound as a binder, the binder has excellent mechanical properties and low viscosity, thereby providing outstanding processibility for the preparation of a glass fiber composite.

The oxetane-epoxy compound of Formula 1 may be prepared by reacting oxetane alcohol with epichlorohydrin. Here, the reaction temperature may range from about −10° C. to about 50° C.

In one embodiment, the binder may include the oxetane-epoxy compound of Formula 1 alone. In another embodiment, the binder may further include a cationic polymerizable compound together with the oxetane-epoxy compound.

The cationic polymerizable compound may include epoxy group-containing compounds, oxetane group-containing compounds, vinyl ether group-containing compounds, caprolactam group-containing compounds, and the like, without being limited thereto. Examples of the cationic polymerizable compound may include glycidyl epoxy resins such as a bisphenol A epoxy resin, bisphenol F epoxy resin, and bisphenol S epoxy resin; 2-hydroxyethyl vinyl ether; diethylene glycol monovinyl ether; 4-hydroxybutyl vinyl ether; diethylene glycol vinyl ether; tri ethylene glycol divinyl ether; cyclohexanedimethanol divinyl ether; cyclohexanedimethanol monovinyl ether; tricyclodecane vinyl ether; cyclohexyl vinyl ether; methoxyethyl vinyl ether; ethoxyethyl vinyl ether; and tetravinyl ether of pentaerythritol.

The cationic polymerizable compound may be present in an amount of about 99 wt % or less, for example, about 0.01 wt % to about 95 wt %, in the binder. The cationic polymerizable compound is preferably present in an amount of about 1 wt % to about 75 wt %, more preferably about 3 wt % to about 70 wt %, still more preferably about 5 wt % to about 65 wt %, in the binder. Within this range, refractive index of the binder can match that of glass fibers, thereby producing a composite sheet having excellent light transmittance.

In one embodiment, a weight ratio of the oxetane-epoxy compound of

Formula 1 to the cationic polymerizable compound may range from about 1:0.05 to about 1:4. Within this range, the binder has excellent heat resistance and permits preparation of a light-transmitting film as the refractive index thereof matches that of the glass fiber. The weight ratio of the oxetane-epoxy compound to the cationic polymerizable compound preferably ranges from 1:0.1 to 1:3.5, more preferably from 1:0.5 to 1:3.

In one embodiment, the difference in refractive index between the binder and the glass filler is about 0.01 or less. In the case of glass fibers having a diameter of 100 nm or more, light scattering at an interface of the glass fibers can cause transmittance reduction. To prevent such transmittance reduction, a difference in refractive index between the binder and the glass filler is about 0.01 or less. The difference in refractive index therebetween is preferably about 0.0001 to 0.007, more preferably about 0.0005 to 0.005. Within this range, the composite sheet can achieve excellent transparency and transmittance.

In one embodiment, the binder may have a transmittance of about 80% to about 99%, preferably about 85% to about 95%. Within this range, the composite sheet can achieve excellent transparency and display quality.

In addition, the binder may have a coefficient of thermal expansion of about 20 ppm/° C. or less, preferably about 0.01 ppm/° C. to about 15 ppm/° C. Within this range, suitable heat resistance for a substrate can be secured.

The oxetane-epoxy compound of Formula 1 is a bifunctional compound and may have a molecular weight/equivalent weight of the reactive functional group of about 110 g/eq or less, preferably about 100 g/eq or less. Such a low molecular weight/equivalent weight of the reactive functional group allows the binder to have a high cross-linking density.

Examples of the glass filler may include glass fibers, glass fiber cloths, glass fabrics, non-woven glass fabrics, glass meshes, glass beads, glass powders, and glass flakes, without being limited thereto. These glass fillers may be used alone or in combination thereof. Preferably, the glass filler is in sheet form, such as glass fiber cloths, glass fabrics, non-woven glass fabrics, glass meshes, etc.

The glass filler may be present in an amount of about 40 parts by weight to about 300 parts by weight based on 100 parts by weight of the binder. Within this range, CTE properties suitable for a substrate can be ensured. Preferably, the glass filler is present in an amount of about 60 parts by weight to about 250 parts by weight based on 100 parts by weight of the binder.

In one embodiment, the composite sheet may further include a cationic initiator. The cationic initiator may include onium-based cationic curing catalysts, aluminum chelate-based cationic curing catalysts, and the like. Examples of the cationic initiator may include an aromatic sulfonium salt, an aromatic iodonium salt, an ammonium salt, an aluminum chelate complex, a boron trifluoride amine complex, etc. The aromatic sulfonium salt may include, for example, hexafluoroantimonate salt; the aluminum chelate complex may include, for example, aluminum ethylacetoacetate diisopropylate and aluminum tris(ethylacetoacetate); and the boron trifluoride amine complex may include, for example, a boron trifluoride monoethylamine complex, a boron trifluoride imidazole complex, and a boron trifluoride piperidine complex. These cationic initiators may be used alone or in combination thereof. The cationic initiator may be present in an amount of about 0.01 parts by weight to about 10 parts by weight, preferably about 0.05 parts by weight to about 5 parts by weight, based on 100 parts by weight of the binder. Within this range, curing reaction of the composite composition can be sufficiently accomplished.

The composite sheet of the present invention may further include antioxidants, UV absorbers, dyes, pigments, coupling agents, other inorganic fillers, and the like, as needed.

The composite sheet of the present invention may be prepared in sheet form by impregnating binder components within the glass filler, followed by cross-linking. The sheet may have a thickness from about 50 µm to about 200 µm, preferably from about 70 µm to about 150 µm.

Figure 2:
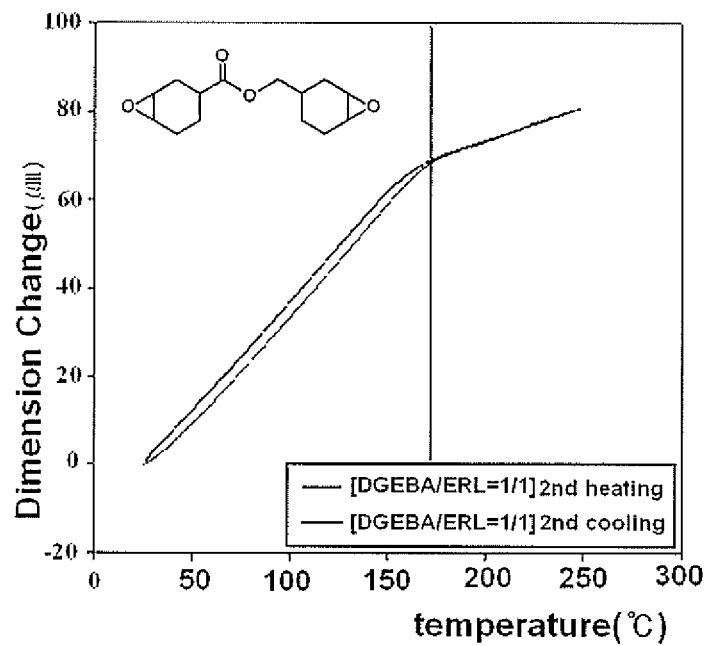
FIG. 2 shows a TMA graph of a composite sheet prepared in Comparative Example 2.

In one embodiment, the composite sheet may have a glass transition temperature of about 150° C. or more, preferably about 200° C. or more, more preferably about 250° C. or more. In another embodiment, the composite sheet may exhibit no glass transition point at about 350° C. or less (Tg-less properties). As used herein, the expression "no glass transition point (Tg-less properties)" means that an inflection point does not appear in data on temperature-dimension change (µm) measured using a TMA (thermo-mechanical analyzer). As shown in FIG. 2, a composite sheet including a conventional binder has an inflection point at 170° C. in TMA data. In contrast, the composite sheet of the present invention does not have any inflection point within the same temperature range. As such, the absence of glass transition point in the process temperature range can ensure excellent heat resistance without deterioration in flexibility. In addition, use of the oxetane-epoxy compound of the present invention as a binder, due to its non aromatic properties and low molecular weight, can result in maintenance of low viscosity, provides excellent wetting properties in preparation of a composite sheet.

Another aspect of the invention relates to a display substrate including the composite sheet. The display substrate may be used as a substrate for display and optical devices, such as liquid crystal display devices (LCDs), color filters, organic EL display devices, solar cells, touch screen panels, etc.

In this case, the composite sheet may further include a hard coat layer, a gas barrier layer, and the like on at least one side thereof. A process of forming these layers can be readily performed by those skilled in the art.

The display substrate may have a coefficient of theithal expansion (a1) of not more than about 30 ppm/° C., preferably not more than about 20 ppm/° C., as measured by a TMA at 5° C./min from 30° C. to 250° C.

For instance, if the binder is present in an amount of about 60 wt % in the composite sheet, the coefficient of thermal expansion (a1) may range from about 20 ppm/° C. to about 25 ppm/° C. In another embodiment, if the binder is present in an amount of about 40 wt % in the composite sheet, the coefficient of thermal expansion (a1) may range from about 10 ppm/° C. to about 15 ppm/° C. In still another embodiment, if the binder is present in an amount of not more than about 30 wt % in the composite sheet, the coefficient of thermal expansion (a1) may be less than about 10 ppm/° C.

The substrate may have a transmittance of about 80% or more, preferably about 85% or more, more preferably about 86% or more at a wavelength of 550 nm.

Now, the present invention will be described in more detail with reference to some examples. However, it should be noted that these examples are provided for illustration only and are not to be construed in any way as limiting the present invention.

Descriptions of details apparent to those skilled in the art will be omitted for clarity.

[Mode for Invention]

EXAMPLES

Preparative Example 1

Preparation of Oxetane-Epoxy

Oxetane alcohol (30 g), epichlorohydrin (34.5 ml), NaOH (17.6 g), and TEBAC (triethylbenzylammonium chloride, 1 mol %, 0.67 g) were placed in a 500 ml flask along with 150 ml of toluene, and then mixed for 5 minutes. Then, after mounting a reflux condenser, the mixture was subjected to refluxing for 3 hours using an oil-bath. After completion of the reaction, the temperature lowered to room temperature, and then the resultant was isolated by filtering through Celite, followed by removing the solvent therefrom using an evaporator, thereby preparing an oxetane-epoxy compound of Formula 1 at a yield of 65%.

[Reaction Formula]

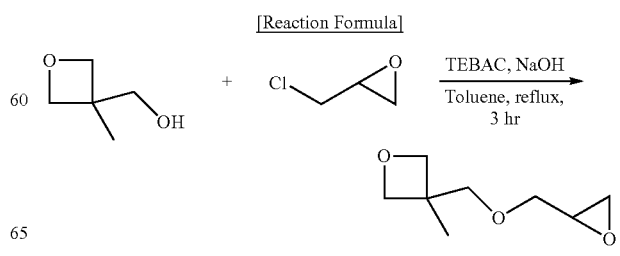

Example 1

Preparation of Composite Sheet 5 g of the oxetane-epoxy obtained in Preparative Example 1, 5 g of diglycidyl ether of bisphenol A, and 0.2 g of a triarylsulfonium hexafluoroantimonate salt were sufficiently mixed. After impregnating the mixture with 10 g of E-glass based glass fibers (Product 3313, Nittobo Co. Ltd.), the resultant was placed between release-treated glass substrates and both sides of the substrate were UV irradiated for 2 minutes, thereby producing a transparent composite sheet (resin content: 50 wt %) having a binder content of 50 wt %. FIG. 1 shows a TMA graph of the prepared composite sheet.

Comparative Example 1

A transparent composite sheet was prepared in the same manner as in Example 1 except that (3-methyloxetan-3-yl) methanol, that is, a monofunctional oxetane represented by Formula 2, was used instead of the oxetane-epoxy prepared in Preparative Example 1. The resultant composite sheet had too low hardness, making it difficult to form a film.

[Formula 2]

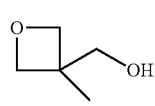

Comparative Example 2

A transparent composite sheet was prepared in the same manner as in Example 1 except that 7-oxa-bicyclo[4.1.0]heptan-3-ylmethyl7-oxa-bicyclo[4.1.0]heptane-3-carboxylate, that is, a di-functional epoxy represented by Formula 3, was used instead of the oxetane-epoxy prepared in Preparative Example 1. FIG. 2 shows a TMA graph of the prepared composite sheet.

[Formula 3]

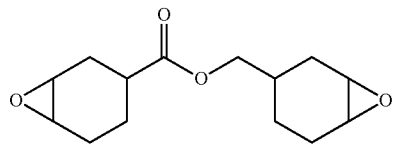

The transparent composite sheets prepared in Example 1 and Comparative Examples 1 and 2 were evaluated as to properties as follows.

(1) Light Transmittance: Light transmittance (%) at a wavelength of 550 nm was evaluated using a UV-Vis spectrometer.

(2) Coefficient of Theilnal Expansion (CTE) and Glass Transition Temperature (Tg): Dimensional change according to temperature was measured using a thermo-mechanical analyzer (Expansion mode, Force 0.05N), and then CTE (ppm/° C.) and glass transition temperature (° C.) of samples were obtained from a sample length variation curve according to temperature.

TABLE 1

| | Light Transmittance @ 550 nm | CTE (ppm/° C.) @ 30~250° C. | Tg (° C.) | Molecular weight/equivalent weight of reactive functional groups (g/eq) |
|---|---|---|---|---|
| Example 1 | 88% | 13 | Tg-less transition | 79 |
| Comparative Example 1 | Impossible to form composite film | — | — | 102 |
| Comparative Example 1 | 88% | 14 @ 30~150° C. | 170° C. | 126 |

As shown in Table 1, it can be seen that the composite sheet prepared in Example 1 maintained initial strength and properties even at a polymer decomposition temperature (at 350° C. or more), thereby not undergoing glass transition. Conversely, the composite sheet of Comparative Example 1 had too low hardness to form a film, and the composite sheet of Comparative Example 2 was increased in coefficient of thermal expansion and had a glass transition temperature of 170° C. Therefore, it could be confirmed that the composite sheet, including the oxetane-epoxy compound as a binder, according to the present invention has excellent heat resistance properties.

Although some embodiments have been described herein, it will be understood by those skilled in the art that these embodiments are provided for illustration only, and various modifications, changes, alterations and equivalent embodiments can be made without departing from the scope of the present invention. Therefore, the scope and sprit of the present invention should be defined only by the accompanying claims and equivalents thereof.

The invention claimed is:

1. A composite sheet comprising:
a binder comprising an oxetane-epoxy compound represented by Formula 1

[Formula 1]

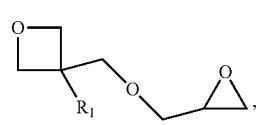

wherein $R_1$ is hydrogen, a methyl group, or an ethyl group; and
a glass filler, wherein a difference in refractive index between the binder and the glass filler is about 0.01 or less.

2. A composite sheet comprising:
100 parts by weight of a binder comprising an oxetane-epoxy compound represented by Formula 1:

[Formula 1]

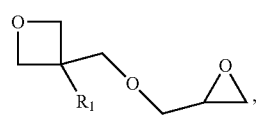

wherein $R_1$ is hydrogen, a methyl group, or an ethyl group; and about 60 parts by weight to about 300 parts by weight of a glass filler.

3. The composite sheet according to claim 1, wherein the glass filler comprises at least one selected from the group consisting of glass fibers, glass fiber cloths, glass fabrics, non-woven glass fabrics, glass meshes, glass beads, glass powders, and glass flakes.

4. The composite sheet according to claim 1, wherein the binder further comprises a cationic polymerizable compound.

5. The composite sheet according to claim 4, wherein the cationic polymerizable compound comprises at least one selected from the group consisting of epoxy group-containing compounds, oxetane group-containing compounds, vinyl ether group-containing compounds, and caprolactam group-containing compounds.

6. The composite sheet according to claim 1, further comprising: a cationic initiator.

7. The composite sheet according to claim 1, wherein the composite sheet has a glass transition temperature of about 200° C. or more.

8. The composite sheet according to claim 1, wherein the composite sheet has a glass transition temperature of about 250° C. or more.

9. A display substrate comprising the composite sheet according to claim 1.

10. The display substrate according to claim 9, wherein the display substrate has a coefficient of thermal expansion of about 30 ppm/° C. or less, as measured using a TMA at 5° C./min from 30° C. to 250° C.

\* \* \* \* \*